United States Patent
Thomas

(10) Patent No.: US 8,137,562 B2
(45) Date of Patent: Mar. 20, 2012

(54) USE OF A COLLOIDAL SUSPENSION OF A CATIONIC POLYMER TO TREAT A SUPPORT FOR MEDICAL USE

(75) Inventor: Michel Thomas, Serezin du Rhône (FR)

(73) Assignee: Gambro Lundia AB, Lund (SE)

( * ) Notice: Subject to any disclaimer, the term of this patent is extended or adjusted under 35 U.S.C. 154(b) by 484 days.

(21) Appl. No.: 12/305,362

(22) PCT Filed: Sep. 6, 2006

(86) PCT No.: PCT/IB2006/002458
§ 371 (c)(1),
(2), (4) Date: Feb. 26, 2009

(87) PCT Pub. No.: WO2007/148147
PCT Pub. Date: Dec. 27, 2007

(65) Prior Publication Data
US 2009/0206038 A1    Aug. 20, 2009

(30) Foreign Application Priority Data
Jun. 22, 2006 (FR) ..................... 06 05571

(51) Int. Cl.
| B01D 11/00 | (2006.01) |
| B01D 39/00 | (2006.01) |
| B01D 63/06 | (2006.01) |
| B01D 63/00 | (2006.01) |
| B01D 67/00 | (2006.01) |

(52) U.S. Cl. ................... 210/645; 210/490; 210/500.37; 210/500.43; 210/321.8; 210/321.75; 264/48; 427/244

(58) Field of Classification Search ............. 210/500.27, 210/490, 500.37, 500.43, 500.23, 321.6, 210/645, 321.75, 321.8; 264/48, 49; 427/244–246
See application file for complete search history.

(56) References Cited

U.S. PATENT DOCUMENTS
4,839,203 A * 6/1989 Davis et al. ................... 427/244
(Continued)

FOREIGN PATENT DOCUMENTS
EP    0 801 953 A1    10/1997
(Continued)

OTHER PUBLICATIONS

Stegmayr Bernd G., "Is There a Future for Adsorption Techniques in Sepsis?", Minireview—Adsorption Technologies, Blood Purification, 2000, vol. 18, No. 2, pp. 149-155.
(Continued)

Primary Examiner — Ana Fortuna
(74) Attorney, Agent, or Firm — Pearne & Gordon LLP

(57) ABSTRACT

The invention concerns a composite support comprising a base support for the treatment of a biological fluid, in which: "the base support is essentially-constituted by a first polymer carrying anionic or anionizable groups;" at least a part of the surface of the base support is coated with a second polymer ionically bonded to the first polymer, the second polymer carrying the cationic or cationizable groups which are capable of forming an ionic bond with the anionic or anionizable groups of the first polymer; in which the second polymer is in the colloidal form and in mixture with a polyacid during application to the support, allowing the composite membrane to adsorb at least one entity containing anionic or anionizable groups by bonding with cationic or cationizable groups of the second polymer.

62 Claims, 5 Drawing Sheets

U.S. PATENT DOCUMENTS

| | | | |
|---|---|---|---|
| 5,630,941 A * | 5/1997 | Burger et al. | 210/490 |
| 5,837,377 A | 11/1998 | Sheu et al. | |
| 6,086,764 A * | 7/2000 | Linder et al. | 210/500.21 |
| 7,056,458 B2 | 6/2006 | Crost et al. | |
| 7,754,646 B2 * | 7/2010 | Trau et al. | 502/233 |
| 2002/0159995 A1 | 10/2002 | Brady et al. | |
| 2003/0021826 A1 | 1/2003 | Crost et al. | |
| 2003/0102262 A1 | 6/2003 | Thomas | |

FOREIGN PATENT DOCUMENTS

| | | |
|---|---|---|
| EP | 0 830 867 A1 | 3/1998 |
| EP | 0 925 826 A1 | 6/1999 |
| EP | 0 993 834 A1 | 4/2000 |
| WO | 96/18498 A1 | 6/1996 |
| WO | 97/33683 A1 | 9/1997 |
| WO | 99/10089 A1 | 3/1999 |
| WO | 01/54802 A1 | 8/2001 |
| WO | 02/45830 A1 | 6/2002 |

OTHER PUBLICATIONS

Nagaki M. et al., "Removal of endotoxin and cytokines by adsorbents and the effect of plasma protein binding", The International Journal of Artificial Organs, vol. 14, No. 1, 1991, pp. 43-50.

Steczko Janusz et al., "Cytokines and Endotoxin Removal by Sorbents and its Application in Push-Pull Sorbent-Based Pheresis: The Biologic-DTPF System", Artificial Organs, vol. 23, No. 4, pp. 310-318, 1999.

Tetta Ciro et al., "Continuous plasma filtration coupled with sorbents", Kidney International, vol. 53, Suppl. 66, 1998, pp. S-186-S-189.

* cited by examiner

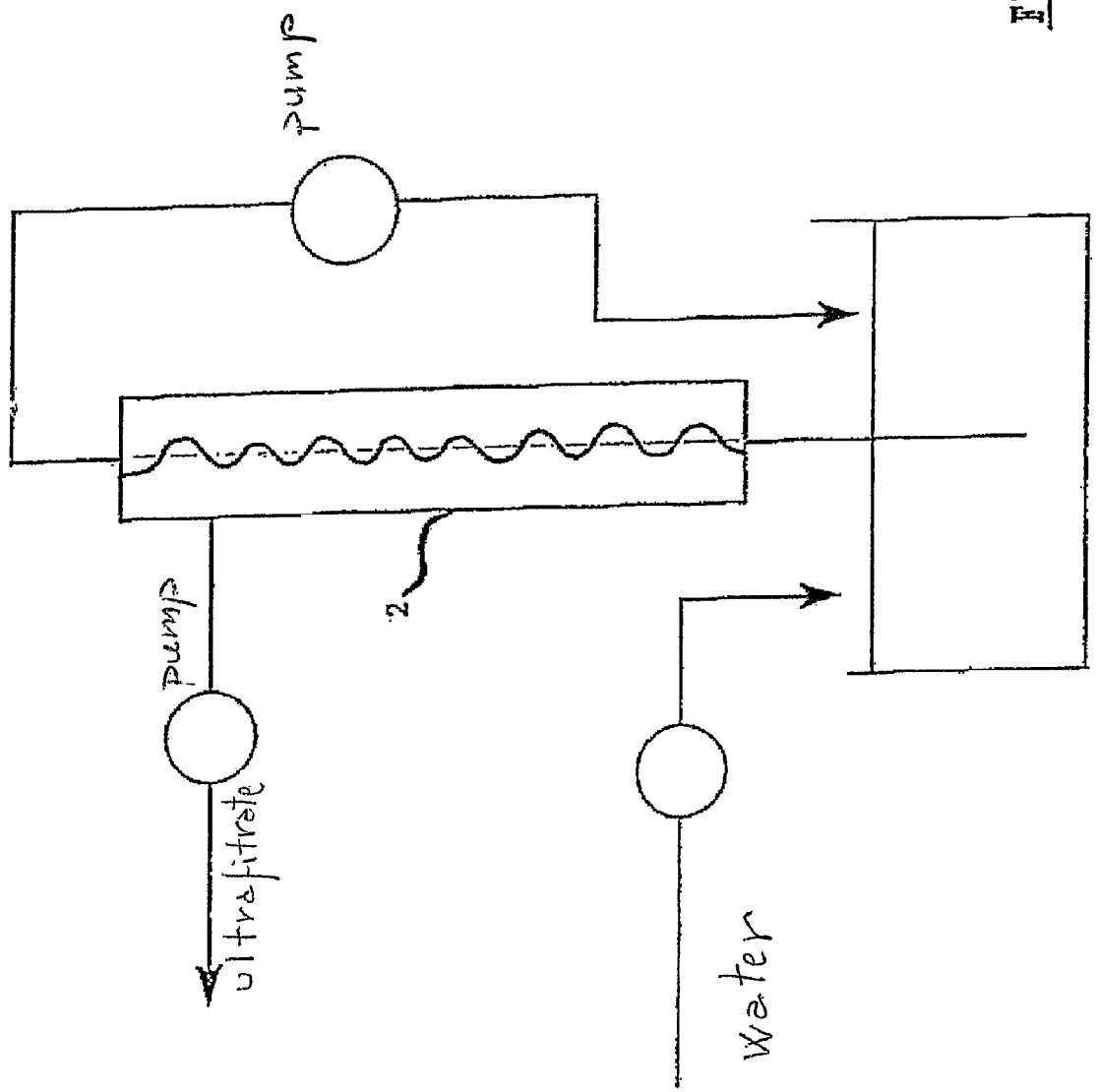

USE OF A COLLOIDAL SUSPENSION OF A CATIONIC POLYMER TO TREAT A SUPPORT FOR MEDICAL USE

FIELD OF THE INVENTION

The present invention relates to the field of supports for medical use for the treatment of biological fluid from a patient or a donor, such as the treatment, for example, of blood or plasma by circulation over or through a support, or the therapeutic treatment of septic syndrome using a support for medical use.

The term "septic syndrome" means the following set of pathologies:
- systemic inflammatory response syndrome (SIRS): characterized by at least two of the following conditions:
  - temperature >38° C. or <36° C.;
  - heartbeat >90/minute;
  - respiration >20/minute;
  - white blood count >12000/µl or <4000/µl;
- sepsis: SIRS with an infection;
- severe sepsis: sepsis with hypotension and lactic acidosis;
- septic shock: severe sepsis with major hypotension and organ dysfunction;
- multi-visceral failure.

This definition is extracted from the "Consensus conference, Sepsis Handbook, R A Balk, Vanderbilt University Medical Center, 2001", which is hereby incorporated by reference.

MORE PRECISE FIELD OF THE INVENTION

More specifically, the invention concerns the use of a suspension to treat a base support for medical use essentially constituted by a first polymer containing anionic or anionizable groups, the suspension being in an acidic medium and comprising a second polymer containing cationic or cationizable groups which are capable of forming an ionic bond with the anionic or anionizable groups of the first polymer, the second polymer being in the colloidal form.

The invention also pertains to a composite support comprising a base support for the treatment of a biological fluid, in which:
- the base support is essentially constituted by a first polymer carrying anionic or anionizable groups;
- at least a part of the surface of the base support is coated with a second polymer ionically bonded to the first polymer, the second polymer carrying the cationic or cationizable groups which are capable of forming an ionic bond with the anionic or anionizable groups of the first polymer;

characterized in that
the second polymer is in the colloidal form, allowing the composite membrane to adsorb at least one entity containing anionic or anionizable groups by bonding with cationic or cationizable groups of the second polymer.

This particular support may be constituted by a composite semi-permeable membrane which can filter blood or plasma by extracorporeal circulation, in particular by dialysis, haemofiltration, haemodiafiltration or by allowing the plasma to be treated by plasmapheresis. This composite membrane may additionally or separately act to adsorb undesirable substances from the treated fluid.

The present invention also pertains to an exchanger comprising:
- a housing defining a first compartment and a second compartment;
  - the first compartment being provided with an inlet and an outlet and intended for the circulation of biological liquid to be treated;
  - the second compartment being intended for the circulation of dialysate or filtrate and being provided with an outlet and optionally with an inlet;
- the two compartments being separated by a composite support in accordance with the invention.

The present invention also pertains to a device for the adsorption of entities contained in a biological fluid comprising:
- a housing provided with an inlet and an outlet and intended for the circulation of biological liquid to be treated;
- a composite support according to the invention.

The term "semi-permeable membrane" means a planar semi-permeable membrane or a bundle of semi-permeable hollow fibres.

The term "exchanger" means an exchanger for the treatment of blood or plasma by extracorporeal circulation which, in general, comprises two compartments separated by a semi-permeable membrane, each being provided with two access points, a first compartment being intended for the circulation of blood or plasma from a patient, and a second compartment being intended for the circulation of used liquid (dialysate, filtrate).

The term "colloidal suspension" means a suspension comprising particles of second polymer dispersed in a continuous phase, preferably aqueous, said suspension containing said polymer in the form of particles with a dimension of 500 nm or less in suspension in the liquid.

The term "polymer in colloidal form" means a polymer in the form of particles with a dimension of less than 500 nm.

This type of exchanger may be used for the treatment of:
- patients suffering from chronic renal insufficiency; and/or
- intensive care patients who may or may not be suffering from renal insufficiency; and/or
- patients with septic syndrome.

The invention also envisages the use of composite membranes and supports of the invention for the manufacture of means for the therapeutic treatment of diseases linked to thrombin, IRCs and afflictions suffered by intensive care patients.

GENERAL COMMENTS/PRIOR ART

An exchanger may be used for two types of treatment of renal insufficiency: chronic treatment and intermittent or continuous acute treatment.

Chronic treatment is intended for patients who are usually waiting for a transplant, in whom the kidneys are not functioning. Such patients undergo three or four sessions per week lasting 4 to 5 hours per session. Examples of exchangers which may be used which can be cited are those sold by the GAMBRO group, comprising an AN69®ST type membrane and forming part of the Nephral®ST (200, 300, 400 and 500) range (hollow fibres with a dimension of 210/253 µm, with an exchange surface of 1.0; 1.3; 1.6 and 2.1 $m^2$).

Intermittent or continuous acute treatment is carried out for patients with severe disease such as trauma, poisoning, septic syndrome, etc. Examples of exchangers used for acute continuous dialysis which may be cited are those sold by the GAMBRO group belonging to the Multiflow (60, 100 and 150) range in Prisma® and/or Prismaflex® sets (AN69® hollow fibres with a dimension of 240/340 µm, and an exchange surface of 0.6; 1.0 and 1.5 $m^2$).

Said exchangers have a negatively charged semi-permeable membrane.

It has been observed that the circulation, especially of blood, in said membrane would cause undesirable contact phase activation. The subject matter disclosed in the Applicant's European patent application EP-A-0 925 626 is aimed at reducing contact phase activation of blood or plasma coming into contact with a negatively charged semi-permeable membrane with an exchanger for the treatment of blood or plasma by extracorporeal circulation comprising a semi-permeable membrane based on polyacrylonitrile carrying bound negative charges. That invention concerned a device for the treatment of blood or plasma by extracorporeal circulation, Comprising a semi-permeable membrane based on polyacrylonitrile carrying bound negative charges wherein, before or after formation of the membrane, at least one neutral or cationic polymer is incorporated into the membrane, in a suitable quantity so as to regulate the overall ionic capacity and the electrokinetic index of the membrane, in a suitable manner. The polymer may be cationic and selected from polyamines, preferably from polyethyleneimines.

At the same time, it was observed that there was a problem with coagulation encountered in the context of the treatment of blood or plasma from a uremic patient in which an extracorporeal blood circuit comprising a semi-permeable membrane exchanger was used. To overcome this problem, the Applicant's International patent application WO-A-0154802 proposed binding, in a stable manner to the surface of semi-permeable membranes essentially constituted by a copolymer of acrylonitrile and at least one anionic and anionizable monomer, an anticoagulation agent which can exert its anticoagulating activity without being leached out into the blood or plasma during treatment by extracorporeal circulation and to reduce the quantity of anticoagulation agent used systemically in the patient during an extracorporeal blood treatment session.

The invention concerned a semi-permeable composite membrane comprising a semi-permeable support membrane and an anticoagulation agent suitable for the treatment of blood or plasma by extracorporeal circulation, said semi-permeable support membrane being essentially constituted by a polyacrylonitrile carrying anionic or anionizable groups; the surface of the semi-permeable support membrane intended to be brought into contact with the blood or plasma was coated in succession with:
  a cationic polymer carrying cationic groups which can form an ionic bond with anionic or anionizable groups of polyacrylonitrile, the cationic polymer (for example polyethyleneimine, PEI), comprising chains of a size which is sufficient not to traverse the semi-permeable support membrane;
  and an anticoagulation agent carrying anionic groups which are capable of forming an ionic bond with cationic groups of said cationic polymer (for example heparin—fractionated or otherwise).

Further, during the treatment of the biological fluid such as blood or plasma, it was observed that certain patients could also suffer from septic syndrome. Said septic syndrome is not necessarily associated with renal insufficiency.

The origin of septic syndrome is infection with bacteria (principally Gram negative) releasing endotoxins (lipopolysaccharides). Such endotoxins induce the synthesis of pro and anti-inflammatory cytokines. The number of nosocomial infections is increasing because of the resistance of bacteria to antibiotic therapy. One of the causes of death during septic syndrome, such as septic shock, may be multi visceral deficiency (MVD) occasioned, inter alia, by disseminated intravascular coagulation (DIVC). The prognosis for MVD accompanied by DIVC is very poor.

Currently, attempts are being made to stem the bacterial infection at the origin of septic syndrome by antibiotic therapy. That technique has limitations due to problems with identification of the strains involved, not to mention the major problem of the resistance of an increasing number of strains to antibiotics, in particular those strains responsible for nosocomial infections.

The battle against septic syndrome also consists of administering anti-inflammatory agents to patients such as anti-II-1, anti-TNF-$\alpha$, anti-endotoxins, anti-PAF (platelet activating factor) or using steroids. Such drugs do not cause significant long term improvements in the survival rate for patients with septic syndrome.

A molecule (protein C, sold under the trade name "XIGRIS") has recently appeared on the market. The cost/benefit ratio of that molecule still has to be quantified.

The quantum of the population suffering from septic syndrome is relatively high, like the population suffering from renal dysfunction, either spontaneous or permanent. Some of those patients may belong to both populations. The invention is applicable to any patient belonging to the entire group of the two populations.

TECHNICAL PROBLEMS AND AIMS OF THE INVENTION

Under these circumstances, one of the essential aims of the invention is the development of novel technical means for therapeutic treatments for septic syndrome, in particular to help or even cure patients and to reduce mortality in said patients in recovery.

Another essential aim of the invention is to provide novel technical means for the therapeutic treatment of septic syndrome, which is substantially more effective and cheaper than known means.

In a further essential aspect, the invention provides novel technical means intended, if necessary at the same time, for the therapeutic treatment of septic syndrome and to purify biological fluids such as blood, plasma or other liquids which may be injected into a patient. The blood treatment may in particular correspond to the treatment of renal insufficiency.

In a yet still further aspect, the invention provides a composite support for the effective adsorption of mediators involved in septic syndrome (endotoxins, cytokines, anaphylatoxins, etc).

In a still further aspect, the invention provides a composite support intended, if necessary at the same time, for the treatment of septic syndrome and to purify biological fluids such as blood, plasma or other liquids which are capable of being injected into a patient.

In a further essential aspect, the invention provides a multifunctional composite support intended, if necessary at the same time, for the treatment of septic syndrome and renal insufficiency (in particular by haemodialysis, ultrafiltration, haemofiltration and/or haemodiafiltration).

In a further aspect, the invention provides a composite support which is effective in adsorbing mediators involved in septic syndrome and if necessary having an anti-thrombogenic nature which can avoid increased systemic anticoagulation in the case of the injection of an anticoagulation agent during treatment via the membrane.

In a further aspect, the invention provides a composite support which is effective in adsorbing mediators involved in septic syndrome and if necessary having an anti-thrombogenic nature allowing the quantity of anticoagulation agents injected into a patient during an extracorporeal blood or plasma treatment session to be significantly reduced or even dispensed with.

In a still further aspect, the invention provides an improvement to the semi-permeable membrane and exchanger of WO-A-01/54802, ensuring an excellent adsorption capacity for undesirable substances contained in the biological fluid intended to be filtered through said membrane.

In a still further aspect, the invention provides an improvement to the semi-permeable membrane and exchanger of WO-A-01/54802, ensuring a larger quantity of anticoagulation agents grafted onto the membrane before the treatment.

DEVELOPMENT OF THE INVENTION

A semi-permeable membrane based on polyacrylonitrile carrying bound negative charges is known in which, before or after forming the membrane, a cationic polymer is incorporated into the membrane in a suitable quantity and manner. The polymer may be selected from polyamines, preferably from polyethyleneimines. Said membrane can eliminate undesirable substances present in the blood of a patient suffering from renal insufficiency.

The inventor sought to provide a medical device having an adsorption capacity for endotoxins and other agents responsible for septic syndrome. It was observed that certain of those agents carry anionic or anionizable groups. The invention elected to operate using a mode of treatment which differed from existing modes (drugs, etc) and to work on a support for medical use which would be rendered capable of adsorbing such agents.

Starting from that choice and the support described in EP-A-0 925 626, the inventor knew of a semi-permeable membrane based on polyacrylonitrile carrying bound negative charges in which, before or after forming the membrane, a cationic polymer was incorporated into the membrane in a quantity that could regulate the overall ionic capacity and the electrokinetic index of the membrane, in a suitable manner. The polymer could be selected from polyamines, preferably from polyethyleneimines (PEI). That membrane could only purify blood.

Further, it was known that protonation of the cationic polymer is encouraged once the pH of the cationic polymer solution is acidic. In fact, the more acidic the pH, the greater the protonation.

However, the inventor observed that under such conditions, the surface density of the cationic polymer at the surface of the membrane comprising an anionic polymer is very low, of the order of 1 mg/m$^2$.

This fact could be attributed to the steric hindrance of the cationic polymer molecules in an acidic medium. In this case, the skilled person, seeking to bind a maximum amount of cationic polymer on the base membrane comprising a polymer carrying anionic groups, would not be led to use the cationic polymer in an acidic medium as while the cationic polymer protonation is suitable, the surface density, in contrast, is too low and the entities containing anionic or anionizable groups could not be grafted to the cationic or cationic groups of the polymer in large quantities.

Alternatively, using a cationic polymer in a basic medium, the inventor observed a higher surface density at a value close to 10 mg/m$^2$, which was insufficient to allow binding of a large number of anionic or anionizable groups of the polymer to be grafted onto the base membrane. Certainly, the surface density increased compared with the acidic medium, but the degree of protonation (and thus the number of free cationic or cationizable groups) was limited.

There was no indication that the pH could be adjusted during manufacture of such a medical device and even less indication regarding selecting between an acidic or basic pH to satisfy the envisaged aims. Consequently, the skilled person was no longer tempted to work with such a support.

Surprisingly, the inventor observed that the use of a solution of a polymer carrying anionic or anionizable groups in the colloidal form and in an acidic medium, in particular by mixing, for example, a solution of polymer carrying anionic or anionizable groups with a solution of organic polyacid in a specific proportion with respect to said polymer, results in a considerable increase in both the quantity of polymer grafted to the surface of the membrane and the availability of free cationic or cationizable groups at the surface of this membrane coating and thus allows a very large quantity of entity (ies) carrying anionic or anionizable groups to be bound.

In subsequent tests, the inventor confirmed that the use of polymer carrying cationic groups employed in the colloidal form does not modify the existing properties of the known support.

Thus, the inventor developed the use of a polymer carrying cationic or cationizable groups on a support for medical use essentially constituted by a polymer carrying anionic or anionizable groups and being in the colloidal form in an acidic medium. The inventor has consequently developed novel therapeutic means constituted by a multifunctional adsorption support grafted in a stable manner and, inter alia, offering effective capacities for endotoxin adsorption and for inhibiting other compounds responsible for coagulation disorder (thrombin), these disorders occurring, for example, in a septic syndrome.

It is assumed that these results are obtained because of particular mutual molecular arrangement of the molecules of the second polymer and/or of the molecules of the second polymer with respect to the molecules of the structure of the first polymer. The particular mutual molecular arrangement of the molecules of the second polymer and/or the quantity of molecules of the second polymer are due at least to the colloidal form of the second polymer.

BRIEF DESCRIPTION OF THE INVENTION

Thus, the inventor achieves the aims mentioned above, inter alia, by dint of the use of a suspension to treat a base support for medical use essentially constituted by a first polymer containing anionic or anionizable groups, the suspension being in an acidic medium and comprising a second polymer containing cationic or cationizable groups which are capable of forming an ionic bond with the anionic or anionizable groups of the first polymer, the second polymer being in the colloidal form.

Said use may result in a composite support comprising a base support for the treatment of a biological fluid, in which the base support is essentially constituted by a first polymer carrying anionic or anionizable groups; at least a part of the surface of the base support is coated with a second polymer ionically bonded to the first polymer, the second polymer carrying cationic or cationizable groups which are capable of forming an ionic bond with the anionic or anionizable groups of the first polymer;
in which the second polymer is in the colloidal form, allowing the composite membrane to adsorb at least one entity containing anionic or anionizable groups by bonding with cationic or cationizable groups of the second polymer.

Said novel support has proved particularly suitable when acting as an adsorbent when it is brought into the presence of or into contact with the blood or plasma from patients with the pathologies discussed above by extracorporeal circulation.

In addition, the portion of the surface of the support may be at least a partially coated with at least one anticoagulation agent carrying anionic or anionizable groups which are capable of forming an ionic bond with the cationic or cationizable groups of the second polymer.

Said novel multifunctional support with as a structure a first polymer coated with a high surface density intermediate layer of a second polymer is integral, in a highly stable manner, with an outer layer of anticoagulation agent.

The invention also concerns a method for manufacturing a composite support for the treatment of biological fluid, said method comprising the following steps:
- a) providing a base support essentially constituted by a first polymer carrying anionic or anionizable groups;
- b) providing a suspension in an acidic medium comprising a second polymer carrying cationic or cationizable groups which are capable of forming an ionic bond with the anionic or anionizable groups of the first polymer, the second polymer being in the colloidal form;
- c) bringing the suspension into contact with at least a portion of the surface of the base support, The use of the invention results in an exchanger comprising:
- a housing defining a first compartment and a second compartment;
- the first compartment being provided with an inlet and an outlet and intended for the circulation of biological liquid to be treated;
- the second compartment being intended for the circulation of dialysate or filtrate and being provided with an outlet and optionally with an inlet;
- the two compartments being separated by a composite support in accordance with the invention.

The invention also concerns a method for manufacturing an exchanger for the treatment of a biological liquid, the exchanger comprising a housing defining a first compartment and a second compartment, the first compartment being provided with an inlet and an outlet and being intended for the circulation of biological liquid to be treated, the second compartment being intended for the circulation of dialysate or filtrate and being provided with an outlet and optionally with an inlet, the two compartments being separated by a base support, the method comprising the following steps:
- a1) providing a base support essentially constituted from a first polymer carrying anionic or anionizable groups;
- a2) assembling the various components of the exchanger, in particular mounting the base support in the housing;
- b1) providing a suspension in an acidic medium containing a second polymer carrying cationic or cationizable groups which can form an ionic bond with the anionic or anionizable groups of the first polymer, the second polymer being in the colloidal form;
- b2) bringing the suspension into contact with at least a first part of the surface of the base support intended to be brought into contact with the liquid to be treated;
- b3) in the case in which steps (b1-b2) are carried out after step a2), rinsing and/or purging the exchanger of the solution containing the second polymer;
- c1) optionally, sterilizing the exchanger thus obtained.

The use of the invention also results in a device for adsorbing entities contained in a biological fluid comprising:
- a housing provided with an inlet and an outlet and intended for the circulation of biological liquid to be treated;
- a composite support in accordance with the invention, contained in the housing.

For this reason, the invention also concerns a method for manufacturing a medical device for the adsorption of entities contained in a biological fluid for the treatment of a biological liquid, the device comprising a housing provided with an inlet and an outlet and being intended for the circulation of biological liquid to be treated, and a composite support in accordance with the invention, the method comprising the following steps:
- a1) providing a base support essentially constituted from a first polymer carrying anionic or anionizable groups;
- a2) assembling the various components of the device, in particular mounting the base support in the housing;
- b1) providing a suspension in an acidic medium containing a second polymer carrying cationic or cationizable groups which can form an ionic bond with the anionic or anionizable groups of the first polymer, the second polymer being in the colloidal form;
- b2) bringing the suspension into contact with at least a first part of the base support intended to be brought into contact with the liquid to be treated;
- b3) in the case in which steps (b1-b2) are carried out after step a2), rinsing and/or purging the adsorption device of the solution containing the second polymer;
- c1) optionally, sterilizing the adsorption device obtained.

Finally, the invention concerns the use of a support in accordance with the invention:
- to treat septic syndrome, in particular by adsorbing endotoxins contained in the biological fluid;
- to purify certain molecules contained in the blood or the plasma by extracorporeal circulation;
- to reduce systemic anticoagulation in a patient during an extracorporeal blood or plasma treatment.

DETAILED DESCRIPTION OF THE INVENTION

In the present text, the numbers given are to an approximation corresponding, for example, to ±10%.

It should be recalled that the invention concerns the use of a suspension to treat a base support for medical use essentially constituted by a first polymer containing anionic or anionizable groups, the suspension being in an acidic medium and comprising a second polymer containing cationic or cationizable groups which are capable of forming an ionic bond with the anionic or anionizable groups of the first polymer, the second polymer being in the colloidal form.

Definition of Second Polymer in the Colloidal Form

The suspension of the second polymer comprises at least one organic polyacid in association with the second polymer, allowing the second polymer to take said colloidal form.

The organic polyacid may be a polycarboxylic acid, in particular comprising at least three carboxylic acid groups, preferably an organic tribasic acid. The polycarboxylic acid in the preferred implementation is citric acid.

Definition of First Polymer

Advantageously, the anionic or anionizable groups of the first polymer are selected from the following groups: sulphonic, phosphonic, carboxylic, sulphuric and phosphoric, and from salts of said groups.

More preferably, the anionic or anionizable groups of the first polymer are acidic sulphonic groups or sulphonic groups in their salt form.

Finally, in a preferred implementation of the invention, the first polymer comprises a polyacrylonitrile, preferably a copolymer of acrylonitrile and sodium methallyl sulphonate.

Use

The suspension may be used:
- to treat the surface of a base support for medical use;

to treat the bulk of a base support for medical use.

The base support used may be in the form of a semi-permeable membrane, beads, a gel or a foam.

Definition of Second Polymer

Still more preferably, the second polymer (P2) is a cationic polymer selected from polyamines, preferably cationic polyaminoacids and/or from polyimines and, more preferably still, from the group comprising: polylysine, polyarginine, polyethyleneimine (PEI), their copolymers and their mixtures.

In a preferred implementation of the invention, polyethyleneimine is the second polymer.

According to one characteristic of the invention, the molecular mass of the second polymer may be greater than the cutoff threshold of the support membrane constituted by the first polymer (P1).

According to a subsequent characteristic of the invention, the second polymer may comprise chains of sufficient size not to traverse the base support. Thus, the second polymer, before being placed into the colloidal form, may comprise chains with sufficient size (steric hindrance) not to traverse the base support comprising the first polymer. This allows it to be bound essentially to the surface of the support essentially constituted by the first polymer, by ionic bonding. Consequently, the quantity of second polymer necessary to treat the surface of the base membrane comprising P1 is moderate when a bulk treatment of the base membrane comprising the first polymer by penetration of the second polymer inside the base membrane comprising the first polymer is not sought. This characteristic is not necessarily useful when a bulk treatment by the second polymer is carried out in addition to the surface treatment of the base support.

The fact that P2 has a molecular mass which is greater than or equal to the cutoff threshold of the membrane may also be an important parameter as regards producing the desired properties in the composite membrane.

Preferably, the second polymer is prepared by ultrafiltration of a solution of the second polymer through a semi-permeable membrane having a cutoff threshold which is greater than or equal to that of a support (for example a semi-permeable membrane) essentially constituted by the first polymer. This allows chains of the second polymer below a certain size corresponding to the porosity of the base support to be eliminated. This preparation mode by ultrafiltration is shown in FIG. 8.

However, this parameter may not be necessary as, when the second polymer (of any molecular size) is taken into colloidal form, the size of the aggregates of polymer increases and the size obtained may then be sufficient not to pass through the base support. This can avoid a step for selecting the molecular size of the second polymer.

Definition of Composite Support

The composite support comprises a base support for the treatment of a biological fluid in which: the base support is essentially constituted by a first polymer carrying anionic or anionizable groups, at least a part of the surface of the base support is coated with a second polymer ionically bonded to the first polymer, the second polymer carrying cationic or cationizable groups which can form an ionic bond with the anionic or anionizable groups of the first polymer, the second polymer being in the colloidal form. The inventor has surprisingly observed that this colloidal form allows the composite membrane to adsorb at least one entity containing anionic or anionizable groups by bonding with cationic or cationizable groups of the second polymer.

The composite support comprises a second polymer which may be in association with an organic polyacid as defined above.

The composite support comprises a first polymer and a second polymer which may be as defined above.

To obtain the colloidal suspension, it is advantageous to carefully select the ratio of the concentration of the second polymer and the organic polyacid.

The ratio of the concentration of the second polymer in the suspension to the concentration of organic polyacid in the suspension is such that it can produce a suspension in the colloidal form. As an example, in the implementation in which the second polymer is polyethyleneimine and the polyacid is citric acid, said ratio of the concentration for PEI and citric acid is in the range 0.9 to 1.1.

Definition of Anticoagulation Agent

The composite support of the invention may comprise said part of the surface of the support at least a partially coated with at least one anticoagulation agent carrying anionic or anionizable groups which are capable of forming an ionic bond with the cationic or cationizable groups of the second polymer.

The anticoagulation agent may comprise at least one compound of the glycoaminoglycanes family having an anticoagulation activity, said anticoagulation agent preferably being selected from the group comprising: non fractionated heparin, fractionated heparin, danaparoids, all heparin derivatives, and mixtures of said products.

Clearly, the anticoagulation agent must not be toxic. Non fractionated heparin is particularly preferred.

The surface concentration of the deposited anticoagulation agent may be in the range 1000 to 30000 IU/m$^2$, preferably in the range 2000 to 8000 IU/m$^2$ of membrane (limits included).

Concentration of Second Polymer

The composite support of the invention has a surface concentration for the second polymer in the colloidal form in the range 15 to 200 mg/m$^2$, preferably in the range 15 to 100 and more preferably in the range 15 to 95 mg/m$^2$.

In a first implementation of the invention, the composite support may have a semi-permeable base membrane as the base support.

Thus, the molecular mass of the second polymer may be greater than the cutoff threshold of the semi-permeable membrane made with the first polymer.

Such a composite support with a base support as a semi-permeable membrane can be termed a composite membrane and will be of use for the purification by extracorporeal circulation of blood or plasma as it comprises at least a first part of the surface intended to be brought into contact with blood or plasma, and a second part of the surface intended to be brought into contact with the dialysate or the filtrate. The first part of the surface of the membrane may be covered by the second polymer in the colloidal form and optionally by an anticoagulation agent carrying anionic or anionizable groups, which can form an ionic bond with the cationic or cationizable groups of the second polymer.

In this mode, at least the second portion of the surface of the membrane intended to be brought into contact with the dialysate or filtrate may be covered with the second polymer in the colloidal form. It may then optionally be covered by an anticoagulation agent carrying anionic or anionizable groups which are capable of forming an ionic bond with the cationic or cationizable groups of the second polymer.

A preferred mode is: the first part of the surface of the membrane is covered by the second polymer in the colloidal form and the anticoagulation agent carrying anionic or anionizable groups which are capable of forming an ionic bond with the cationic or cationizable groups of the second polymer, and in combination, the second part of the surface of the membrane is covered by the second polymer in the colloidal form.

The second polymer in the colloidal form for the second part of the surface may have a molecular size which is over a certain threshold.

Alternatively, it is also possible to envisage covering the second part of the surface with the second polymer which is not in the colloidal form and/or which has a molecular size above a cutoff threshold for the membrane of the first polymer.

The composite membrane coated solely with a second polymer in the colloidal form on the first surface ("blood face") and on the second surface ("filtrate or dialysate face") is a membrane which is termed a "colloidal bi-face" membrane.

Said multifunctional membrane can adsorb endotoxins which are the source of septic syndrome, it can reduce contact phase activation, and it can adsorb an anticoagulation agent grafted on during manufacture just before blood treatment or injected into the patient during the blood treatment.

The semi-permeable membrane is a stack in the form of planar membranes, or it is constituted by a bundle of hollow fibres.

In the case of a bundle of hollow fibres, the interior surface of the hollow fibres is the first part of the surface intended to come into contact with the blood or plasma and the exterior surface of the hollow fibres is the second part of the surface intended to be brought into contact with the filtrate or the dialysate.

In the context of the preferred implementation of a semi-permeable membrane, the first polymer may, for example, be a copolymer of acrylonitrile and sodium methallylsulphonate, such as the copolymer with the trade name AN69 manufactured by GAMBRO INDUSTRIES, with which the best performances have been achieved. In the same manner, the second polymer is preferably a PEI, since the anticoagulation agent is heparin. The composite semi-permeable membrane of this preferred implementation of the invention has an effective anticoagulation activity during a treatment or plasma blood session using extracorporeal circulation (ECC). Further, the anticoagulation agent (for example heparin) is bound in a stable manner to the structure of the first polymer covered with the second polymer in the colloidal form.

In a second alternative implementation to a semi-permeable membrane as the base support, the support may comprise a base support constituted by one of the following forms: an assembly of beads, a foam or a gel.

A base support (beads, foam, sponge, for example) with a variable porosity can be envisaged.

The base support in this second implementation is essentially constituted by the first polymer.

In a first implementation, said base support may be manufactured in a first step and then treated during a second step with the suspension of the second polymer in the colloidal form. Treatment with the suspension may be carried out on the surface, more particularly on the "apparent surface" (i.e. the apparent visible surface) but also optionally on the "developed surface" (i.e. on the apparent surface and the surface presented by the pores inside the base support).

In the case in which the apparent surface alone is treated, this is termed the surface treatment of the first polymer. In the case in which the apparent and developed surfaces are treated, this is termed the bulk treatment of the first polymer.

In a second alternative implementation, said support may be manufactured by simultaneously mixing the first polymer with a suspension of the second polymer in the colloidal form. This is termed the bulk treatment of the first polymer: this mode can bind the second polymer both to the apparent surface and to the developed surface.

Such a support (in one of the two implementations) is placed in a housing comprising an inlet to introduce the biological fluid to be treated and an outlet to allow the treated fluid to leave. Said support is capable of adsorbing entities of the fluid carrying anionic or anionizable groups by ionic bonding.

In this mode, in addition to being on the apparent surface, the second polymer in the colloidal form may also be present in the bulk of the base support, for example in the bulk of the foam or in the bulk of the beads.

In this case, the quantity of bound second polymer in the colloidal form will depend on the porosity of the support.

Functional Definitions of the Support

The support may also be defined through its capacity to adsorb endotoxins.

The composite support of the invention has an endotoxin adsorption capacity (*Escherichia Coli* O55:B5, expressed in $EU/m^2$ and measured using method M described below), of 500 $EU/m^2$, preferably 1500 $EU/m^2$ or more.

In a preferred mode, the adsorption capacity of the endotoxins is in the range 2000 to 5000 $EU/m^2$.

Method M: circulation (closed circuit, 500 ml at flow rate of 300 ml/min) in the blood compartment of a hollow fibre dialyzer, of physiological serum containing 10 EU/ml of Escherichia Coli O55: B5 endotoxins. Endotoxin assay by Limulus LAL test.

In addition to the adsorption capacity, the binding or grafting stability of the anticoagulation agent on the structure of the first polymer (P1) coated with the second polymer (P2) is also one of the essential parameters of the present invention.

This anticoagulation agent grafting stability may be established by means of the coagulation time given by the CKT.

Thus, the support of the invention preferably has a CKT which does not significantly increase (approximately 10%) with respect to the initial value over at least 6 hours in a test during an ECC (extracorporeal circulation) as described in the description.

This test for determining the coagulation time (CKT, cephalin kaolin time) is as follows:

The CKT is determined using an assay kit sold under the trade name C K PRESTO by DIAGNOSTICA STAGO.

The CKT determines the extension in the coagulation time of a citrated plasma caused by a deficiency of certain coagulation factors or by the presence of an anticoagulation agent such as heparin. In this latter case, the extension of the coagulation time is proportional to the quantity of heparin present.

Determining the CKT can thus indicate the level of anticoagulation agent in the blood. The method for measuring this coagulation time (expressed in seconds) is known; it is carried out after recalcification and adding an activator. As an example, a hollow fibre dialyzer (trade name FILTRAL 16 produced by GAMBRO INDUSTRIES, France) is used, provided with a useful membrane surface area of 1.6 m of AN69 (P1=copolymer of acrylonitrile and sodium methallyl) and coated on its two faces with P2=PEI then with anticoagulation agent=heparin.

An extracorporeal blood circuit including the dialyzer is then connected to the vascular system of a sheep. No anticoagulation agent is injected into the sheep's blood.

The CKT is measured during the entire duration of the circulation.

Definition of Composite Support by the Method by which it is Obtained:

The properties of the composite support of the invention are at least partially determined by the method by which it is obtained, which may be assimilated with at least one surface treatment.

The method for manufacturing a composite support for the treatment of biological fluid comprises the following steps:
a) providing a base support essentially constituted by a first polymer carrying anionic or anionizable groups;
b) providing a suspension in an acid medium comprising a second polymer carrying cationic or cationizable groups which are capable of forming an ionic bond with the anionic or anionizable groups of the first polymer, the second polymer being in the colloidal form;
c) bringing the suspension into contact with at least a part of the surface of the base support.

The first polymer and the second polymer may be as defined above.

In accordance with one characteristic of the invention, the second polymer is obtained in the colloidal form by a step for mixing a first solution comprising the second polymer with a second solution comprising at least one organic polyacid. Said polyacid may be as defined above.

According to one characteristic of the invention, the ratio of the concentration of the second polymer in the suspension to the concentration of organic polyacid in the suspension is such that it can produce a suspension in the colloidal form.

If the second polymer is polyethyleneimine and the polyacid is citric acid, said ratio of the concentration for PEI and citric acid is in the range 0.9 to 1.1.

In accordance with one characteristic of the invention, the method comprises, after step c), a step d) which is as follows: bringing at least a portion of said part of the surface of the base support into contact with a solution comprising at least one anticoagulation agent carrying anionic or anionizable groups which are capable of forming an ionic bond with the cationic or cationizable groups of the second polymer to bind an anticoagulating coating onto a portion of said part of the surface of the support coated with the second polymer.

Said step d) is carried out just before using a composite support for the treatment of biological fluid (extemporaneously) or during the manufacture of the composite support.

When the anticoagulation agent is grafted just before the treatment, it may be carried out during rinsing or priming of the filter by passing a preparation liquid through the entire circuit composed of composite support.

In accordance with a further characteristic of the invention, the method comprises, as a final optional manufacturing step, a step for sterilization of the support. Sterilization may be gamma sterilization or sterilization using ethylene oxide which may or may not be preceded by gamma irradiation, or using techniques which are well known to the skilled person.

The first solution comprising the second polymer may be prepared by ultrafiltration of a solution of the second polymer through a semi-permeable membrane to eliminate chains of the second polymer with a size which is less than or equal to the size corresponding to the porosity of the base support.

This step is carried out before the step for mixing with the second acid solution.

Further, treatment by the suspension in an acidic medium of the second polymer in the colloidal form may be carried out in at least a part of the bulk of the base support.

In the context of the invention, the term "colloidal suspension" means a suspension comprising particles of second polymer dispersed in a continuous phase, preferably aqueous. The size of said particles of second polymer (mean diameter) is 500 nm or less; as an example, in the range 10 to 500 nm, preferably in the range 50 to 200 nm, or even in the range 80 to 120 nm, for example of the order of 100 nm.

The particular conditions for the composite support manufacturing method are as follows:
the second polymer (P2) comprises PEI and the organic polyacid comprises citric acid. One and/or the other of the following conditions is applied:
i. concentration of PEI: 0.1 to 10 g/l, preferably 0.2 to 1;
ii. ratio of PEI/citric acid concentrations by weight: 0.7 to 1.3, preferably 1.0.
P2 comprises PEI and the anticoagulation agent comprises heparin. One and/or the other of the following conditions is applied:
concentration of heparin: 5 to 200 IU/ml, preferably 10 to 100;
the liquid medium in step d) is an aqueous medium, containing constituents selected from the group comprising: water, water+salt, acidified water, pH 3 to 7;
at least one of steps c) and step d) respectively is carried out by continuously circulating the liquid medium containing P2 and the anticoagulation agent respectively over at least one of the surfaces of the semi-permeable base support membrane of the first polymer (P1) to be coated and in which at least one of the following conditions is implemented:
for step c):
i. prior mixing of the 2 solutions or in line mixing just before treatment;
ii. treatment flow rate: 50 to 500 ml/min, preferably 100 to 200;
iii. open circuit or closed circuit (uni- or bi-directional);
iv. duration: 1 to 30 min, preferably 5 to 10;
for step d):
i. flow rate: 50 to 500 ml/min;
ii. open or closed circuit, uni or bi-directional
iii. duration: 1 to 30 min, preferably 5 to 10.

In the case in which P1 is a copolymer of polyacrylonitrile and sodium methallylsulphonate, the structure based on P1 may optionally be de-glycerined before the surface treatment aimed at binding the P2 coating in step c) and the anticoagulation treatment in step d). For "deglycerination", an aqueous liquid is circulated.

Multifunctional Exchanger

The invention also envisages an exchanger comprising:
a housing defining a first compartment and a second compartment;
the first compartment being provided with an inlet and an outlet and intended for the circulation of biological liquid to be treated;
the second compartment being intended for the circulation of dialysate or filtrate and being provided with an outlet and optionally with an inlet;
the two compartments being separated by a composite support in accordance with the invention.

In accordance with a further characteristic of the invention, the compartments of the exchanger are also separated by a setting mass based on an appropriate adhesive composition intended to form, depending on the case:
i) a cylindrical partition separating the two compartments comprising, as a support, a permeable membrane in the form of a bundle of hollow fibres;
ii) a seal in said device comprising, as a support, a semi-permeable membrane in the form of a stack of planar membranes.

Advantageously, the exchanger of the invention has a volume or an exchange surface of about 200 cm² or more and less than about 4 m², preferably for an adult in the range from about 0.6 m² to 2 m².

Preferably, the exchanger which comprises the composite semi-permeable membrane, i.e. the support of the invention, is sterilized and ready to use. Thus, it does not require any special manipulation by the consumers.

Method for Producing the Exchanger

The present invention also pertains to a method for manufacturing an exchanger for the treatment of a biological liquid, the exchanger comprising a housing defining a first compartment and a second compartment, the first compartment being provided with an inlet and an outlet and being intended for the circulation of biological liquid to be treated, the second compartment being intended for the circulation of dialysate or filtrate and being provided with an outlet and optionally with an inlet, the two compartments being separated by a base support, the method comprising the following steps:

a1) providing a base support essentially constituted from a first polymer carrying anionic or anionizable groups;

a2) assembling the various components of the exchanger, in particular mounting the base support in the housing;

b1) providing a suspension in an acidic medium containing a second polymer carrying cationic or cationizable groups which can form an ionic bond with the anionic or anionizable groups of the first polymer, the second polymer being in the colloidal form;

b2) bringing the suspension into contact with at least a first part of the surface of the base support intended to be brought into contact with the liquid to be treated;

b3) in the case in which steps (b1-b2) are carried out after step a2), rinsing and/or purging the exchanger of the solution containing the second polymer P2;

c1) optionally, sterilizing the exchanger thus obtained.

step b3) may optionally be followed by rinsing the semi-permeable membrane to eliminate excess non-bound second polymer.

According to a further characteristic of the method, after steps b), a step c0) may be inserted for bringing at least one solution of an anticoagulation agent into contact in a liquid medium with at least a portion of the part of the surface of the base support coated with the second polymer in the colloidal form to bind an anticoagulation coating onto the surface of the support coated with second polymer in the colloidal form; step c0) may be carried out before or after step a2).

In the case in which step c0) is carried out after step a2), the exchanger may be purged of the solution containing the anticoagulation agent.

Step c0) may be carried out during manufacture before sterilization c1) or subsequent to manufacture and just before use.

Optionally, the semi-permeable membrane may be rinsed to eliminate excess non-bound anticoagulation agent.

The first and second polymers may be as defined above.

The following operating condition may be envisaged: P2 is mixed with at least one organic polyacid (polycarboxylic), preferably an organic tribasic acid (or more preferably, citric acid).

Optionally, the planar membrane or the bundle of hollow fibres is glycerined at the end of step a1), hence the need to deglycerinate before undertaking step b2) defined above.

Optionally, the semi-permeable membrane is rinsed to eliminate excess bound cationic polymer P2. Optionally, the semi-permeable membrane is rinsed to eliminate excess non-bound anticoagulation agent.

Optionally, the semi-permeable membrane is reglycerinated, depending on the case.

In the context of the invention, sterilization of the exchanger, with no effect on the composite semi-permeable membrane, may be sterilization by irradiation, for example gamma irradiation, or by sterilization with ethylene oxide, and may be carried out before or after depositing the anticoagulation agent.

Additional characteristics of the exchanger and its manufacturing method will be deduced from data concerning the use and the composite support of the invention.

Adsorption Device

In accordance with a further aspect, the invention concerns a device for adsorbing entities contained in a biological fluid comprising:

a housing provided with an inlet and an outlet and intended for the circulation of biological liquid to be treated;

a composite support in accordance with the invention contained in the housing.

The invention concerns a method for manufacturing a medical device for the adsorption of entities contained in a biological fluid for the treatment of a biological liquid, the device comprising a housing provided with an inlet and an outlet and being intended for the circulation of biological liquid to be treated, a composite support in accordance with the invention, the method comprising the following steps:

a1) providing a base support essentially constituted from a first polymer carrying anionic or anionizable groups;

a2) assembling the various components of the device, in particular mounting the base support in the housing;

b1) providing a suspension in an acidic medium containing a second polymer carrying cationic or cationizable groups which can form an ionic bond with the anionic or anionizable groups of the first polymer, the second polymer being in the colloidal form;

b2) bringing the suspension into contact with at least a first part of the base support intended to be brought into contact with the liquid to be treated; b3) in the case in which steps (b1-b2) are carried out after step a2), rinsing and/or purging the adsorption device of the solution containing the second polymer;

c1) optionally, sterilizing the adsorption device obtained.

Additional characteristics of the adsorption device and its manufacturing method can be deduced from data concerning the use and the composite support of the invention.

Therapeutic Use

In a further aspect, the invention concerns:

the use of a support or an exchanger in accordance with the invention to treat septic syndrome, in particular by adsorption of endotoxins contained in the biological fluid;

the use of a support or an exchanger in accordance with the invention to purify certain molecules contained in the blood or plasma by extracorporeal circulation;

the use of a support or an exchanger of the invention to reduce systemic coagulation in a patient during an extracorporeal blood treatment in particular by adsorption by the support of an anticoagulation agent injected into the blood or plasma. This effect is due to the non thrombogenic nature of the composite support because of the pre-fixed anticoagulation agent or the adsorption capacity of the anticoagulation agent injected into the patient during treatment.

Other characteristics and advantages of the invention will become apparent from the following examples.

Reference will also be made to the accompanying drawings and Figures in which:

FIG. 1 shows the adsorption kinetics of endotoxins (lipopolysaccharides, LPS) during an in vitro comparative test with human plasma for an exchanger of the invention (Example 1) and for a prior art exchanger (M100);

FIGS. 2 to 6 respectively show the systemic vascular resistance SVR, the mean pulmonary arterial pressure MPAP, the quantity of injected crystalloid solution, the concentration of lactate and of acidosis respectively for control pigs treated using the control (M100) type exchanger and for pigs treated using an exchanger comprising the semi-permeable membrane of the invention;

and FIG. 7 shows the amount of the various cytokines measured at the end of treatment for the control pigs M100 and for pigs treated with the exchanger of the invention (Example 1);

FIG. 8 shows the circuit used to prepare PEI with a molecular size above a certain threshold;

EXAMPLES

Example 1

Manufacture of Product of Example 1

Figure 1:
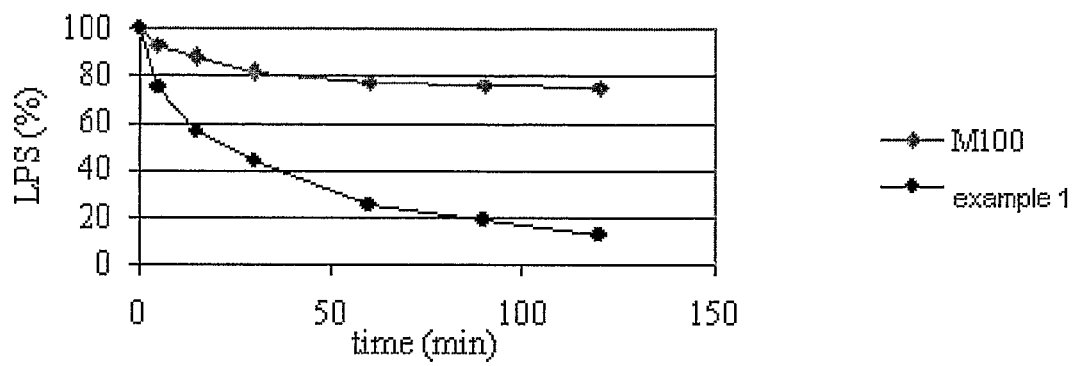
Figure 2:
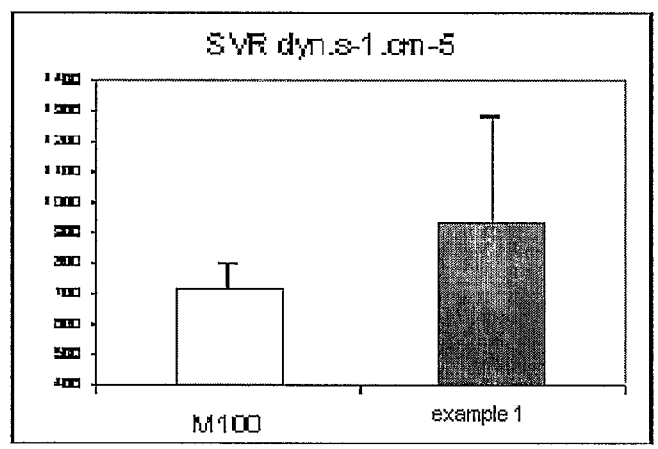
Figure 3:
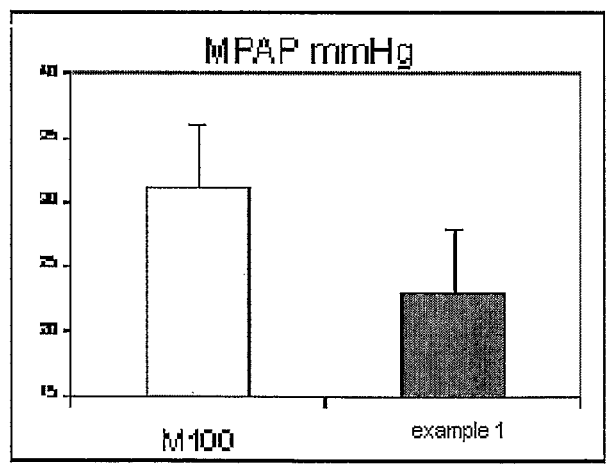
Figure 4:
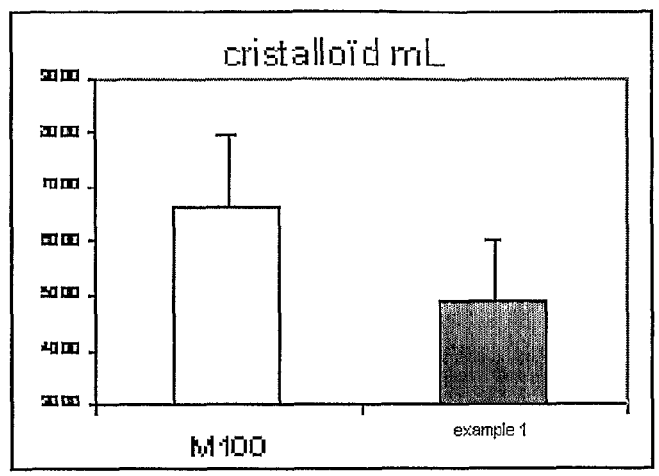
Figure 5:
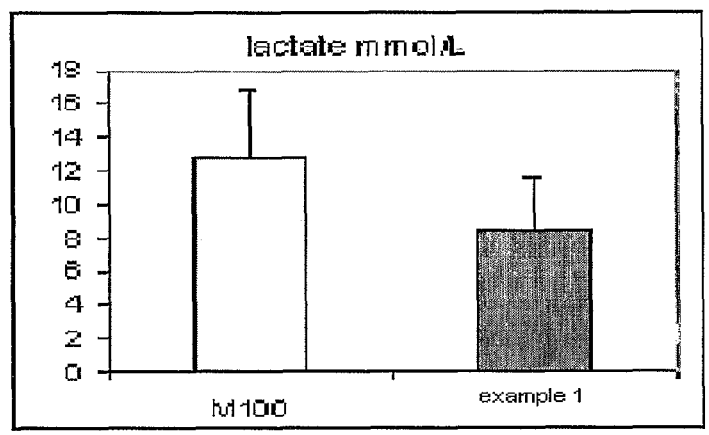
Figure 6:
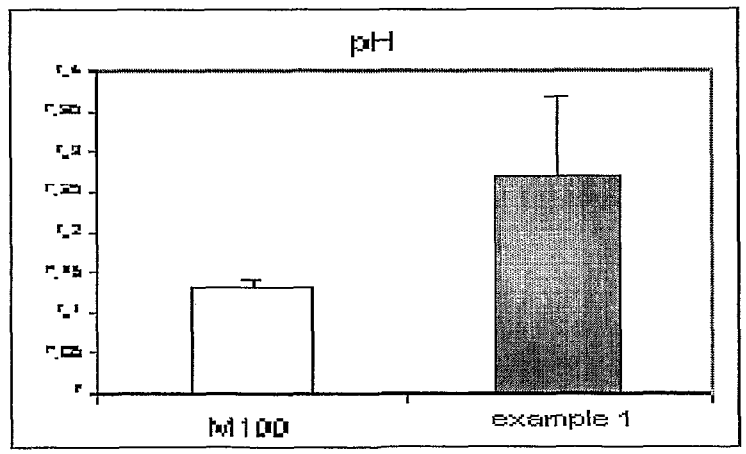

1. Preparation of a solution 1 containing:
   high molecular mass polyethyleneimine (PEI), 1 g/l;
   citric acid, 1 g/l;
   solvent: water.
   The solution was in the colloidal form.
   See FR-B-2 804 328 in particular for the preparation and characterization of this PEI. Said method for preparing a cationic polymer, in this case a polyethyleneimine (PEI), aiming at eliminating, by fractionation, the smallest chains of polymers (with a low steric hindrance) which may penetrate into the pores of the semi-permeable membrane to be treated and traverse it. FIG. 8 shows the procedure for preparing PEI which comprises the following steps: a-preparation, in a tank 1, of a solution of 1.5 litres of a solution of PEI with a mass average molecular mass of 750 kdalton (LUPASOL P from BASF), 50 g per litre, in distilled water; b-circulation, in a closed circuit, of said solution in the blood compartment of a dialyzer 2 with hollow fibres (trade name FILTRAL 16, manufactured by GAMBRO INDUSTRIES, France) provided with a membrane (useful surface 1.6 m$^2$) formed from AN69 (copolymer of acrylonitrile and sodium methallylsulphonate) at a flow rate of 300 ml per minute; c-simultaneously with step b, ultrafiltration at a flow rate of 60 ml per minute, adding water to tank 1 at the same flow rate.

2. Preparation of solution 2 containing:
   non fractionated heparin in a concentration of 128 IU/ml (IU=anti Xa activity);
   solvent: water.

3. Surface treatment: the internal compartment (in contact with the blood) of a Multiflow 100 (M100) type product was treated as follows:
   circulation of water at a flow rate of 150 ml/min for 5 min;
   circulation of solution 1;
      flow rate 300 ml/min, 2.5 min in direction 1 of diagram;
      flow rate 300 ml/min, 2.5 min in direction 2.
   circulation of solution 2
      flow rate 300 ml/min, 2.5 min in direction 1;
      flow rate 300 ml/min, 2.5 min in direction 2
   purge of internal compartment with air (1 min with an inlet pressure of 400 mmHg).

4. Sterilization of products by gamma irradiation (30 kGy).
   After sterilization, the product was characterized.

Adsorption Capacity of Endotoxins of Example 1:

Methods: circulation (closed circuit, 500 ml at a flow rate of 300 ml/min) in the blood compartment, of heparinated human plasma, 10 IU/ml containing 1 EU/ml of Escherichia Coli O55: B5 endotoxins.

Description of Test:
   At regular time intervals, the amount of endotoxins in the plasma was measured (LAL test) for a negative control constituted by an M100 exchanger not treated with PEI and heparin in accordance with the invention and for the exchanger of the invention the preparation of which is described above. The results are shown in FIG. 1.

In vivo test of Example 1:
Method:
   35 kg pigs
   general anaesthesia (propofol, 3 mg/kg);
   perfusion of pseudomonas aeruginosa (5.108 CFU/ml, 0.3 ml/min, 20 kg);
   treatment of septic shock obtained by administration of crystalloids in order to maintain a mean arterial pressure of 70 mmHg;
   4 pigs for each type of product (M100 and product of the invention).

Results:
Haemodynamics
   SVR: systemic vascular resistance: reduces with shock; an increase is a sign of improvement;
   MPAP: mean pulmonary arterial pressure: increases during shock; a reduction is favourable;
   crystalloid: solution injected to compensate for drop in arterial pressure: low use is a positive sign;
   lactate and pH: indication of acidosis induced by shock: a reduction in lactates, which is associated with an increase in pH, is a positive sign.

The results are given in FIGS. 2 to 6, from which it will be observed that all of the haemodynamic parameters move in the direction of an improvement in the condition of the animal.

Figure 7:
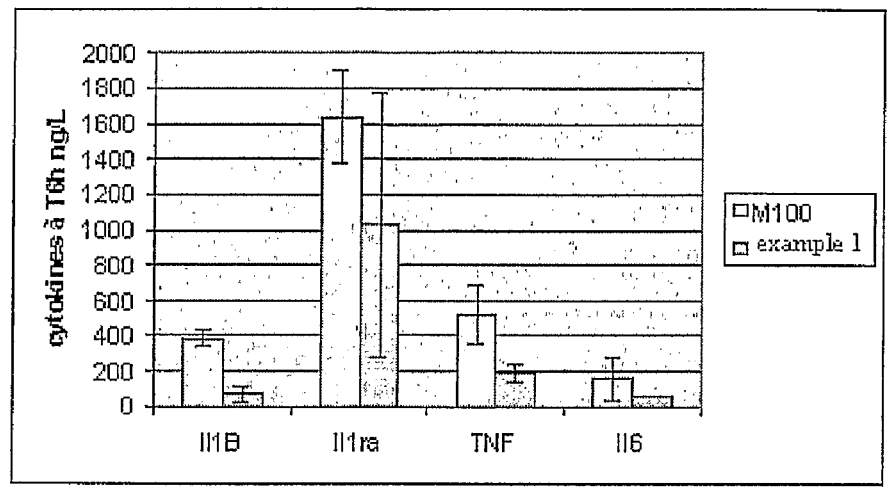

As a supplemental result of this test, FIG. 7 shows the blood concentration of cytokines compared at the end of treatment. These results demonstrate that the concentrations of the 4 cytokines measured, namely Il1B, Il1ra, TNF and Il6, are advantageously lower in the pigs treated in accordance with the invention.

Example 2

Manufacture of Product of Example 2

1. Preparation of a solution 1 containing:
   polyethyleneimine with a high molecular mass (PEI) 0.2 g/l. For the preparation and characterization of this PEI, see FR-A-2 804 328 and the description in Example 1 of the present application;
   citric acid, 0.2 g/l;
   solvent: water.
   The solution was in the colloidal form.

2. Preparation of a solution 2 containing:
   non fractionated heparin in a concentration of 100 IU/ml (IU=anti Xa activity);
   solvent: water.

3. Surface treatment: a hollow fibre type exchanger with a useful surface of 1.5 m (Multiflow 150, M150) was treated as follows:
   circulation of water in the internal (blood) and external (dialysate) compartments at a flow rate of 150 ml/min for 5 min (deglycerination);
   circulation of solution 1 in the internal (blood) and external (dialysate) compartments;
      flow rate 300 ml/min, 2.5 min in direction 1;
      flow rate 300 ml/min, 2.5 min in direction 2.
   circulation of solution 2 in internal compartment (blood)
      flow rate 300 ml/min, 2.5 min in direction 1;
      flow rate 300 ml/min, 2.5 min in direction 2;
   circulation of an aqueous glycerol solution (60% glycerol) in internal (blood) and external (dialysate) compartments;
   purge of both compartments with air (1 min with an inlet pressure of 400 mmHg).
4. Sterilization of products with ethylene oxide.

After sterilization, the product was characterized as regards endotoxin adsorption:

Adsorption Capacity of Endotoxins of Example 2:

Methods: circulation (closed circuit, 500 ml, at a flow rate of 300 ml/min for 2 hours) in the blood compartment of water containing 10 EU/ml of Escherichia Coli O55: B5 endotoxins.

Results:

|  | Adsorption of endotoxins $EU/m^2$ |
|---|---|
| Reference, Multiflow 150 | <100 |
| Example 2 | 2600 |

It will be observed that the endotoxin adsorption capacity for Example 2 is much higher than that of the reference product which was not treated in accordance with the invention.

Example 3

Manufacture of Product of Example 3

1. Preparation of a solution 1 containing:
   polyethyleneimine with a high molecular mass (PEI), 0.5 g/l. For the preparation and characterization of this PEI, see patent FR2 804 328 and the description in Example 1 of the present application;
   citric acid, 0.5 g/l;
   solvent: water.
The solution was in the colloidal form.
2. Preparation of solution 2 containing:
   non fractionated heparin in a concentration of 50 IU/ml (IU=anti Xa activity);
   solvent: water.
3. Surface treatment: a Multiflow 150 (M150) type product was treated as follows:
   circulation of water in the internal (blood) and external (dialysate) compartments at a flow rate of 150 ml/min for 5 min;
   circulation of solution 1 in the internal (blood) and external (dialysate) compartments;
      flow rate 300 ml/min, 2.5 min in direction 1;
      flow rate 300 ml/min, 2.5 min in direction 2.
   circulation of solution 2 in internal compartment (blood)
      flow rate 300 ml/min, 2.5 min in direction 1;
      flow rate 300 ml/min, 2.5 min in direction 2
   a circulation of an aqueous glycerol solution (60% glycerol) in internal (blood) and external (dialysate) compartments;
   purge of both compartments with air (1 min with an inlet pressure of 400 mmHg).
4. Sterilization of products with ethylene oxide.

After sterilization, the product was characterized as regards endotoxin adsorption:

Adsorption Capacity of Endotoxins of Example 3:

Circulation (closed circuit, 2000 ml, at a flow rate of 300 ml/min for 2 hours) in the blood compartment of the product of water containing 10 EU/ml of Escherichia Coli O55: B5 endotoxins.

Results of Example 3:

|  | Adsorption of endotoxins $EU/m^2$ |
|---|---|
| Reference, Multiflow 150 | <100 |
| Example 3 | 7380 |

It will be observed that the endotoxin adsorption capacity for Example 3 is much higher than that of the reference product which was not treated in accordance with the invention, and also higher than that of Example 2 as more PEI had been adsorbed.

Figure 9:
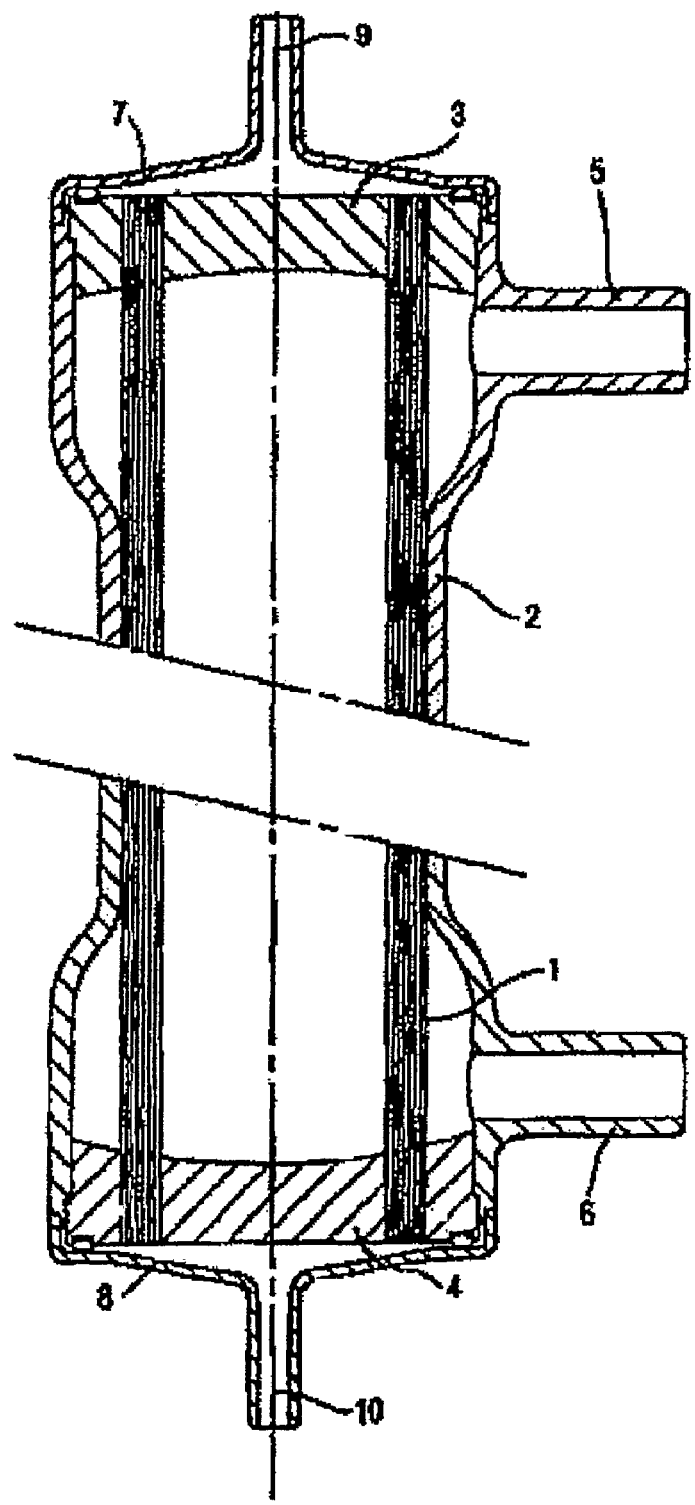
FIG. 9 shows an exchanger in accordance with the invention.

As will be observed in FIG. 9, an exchanger in accordance with the present invention comprises a semi-permeable membrane such as a bundle of hollow fibres (1) which is disposed in a tubular housing (2) in which it is secured at its two ends by partition in the form of a disk (3, 4). In addition to the fact that the fibres are bonded to each other, the disks act to define in the tubular housing (2) a sealed compartment to which two connectors (5, 6) perpendicular to the axis of the housing (2) provide access. A cap (7, 8) is fixed at each end of the housing (2), said cap comprising an 8 axial access connector (9, 10). The two connectors (9, 10) are symmetrical. The blood compartment of the device of the invention is constituted by the interior space defined between each bonding disk (3, 4) and the cap (8, 9) closing the corresponding end of the tubular housing (2), and by the interior of the hollow fibres. The compartment intended for the filtrate is constituted by the space accessed by the two connectors (5, 6) perpendicular to the axis of the housing (2) and includes the exterior of the hollow fibres.

Figure 10:
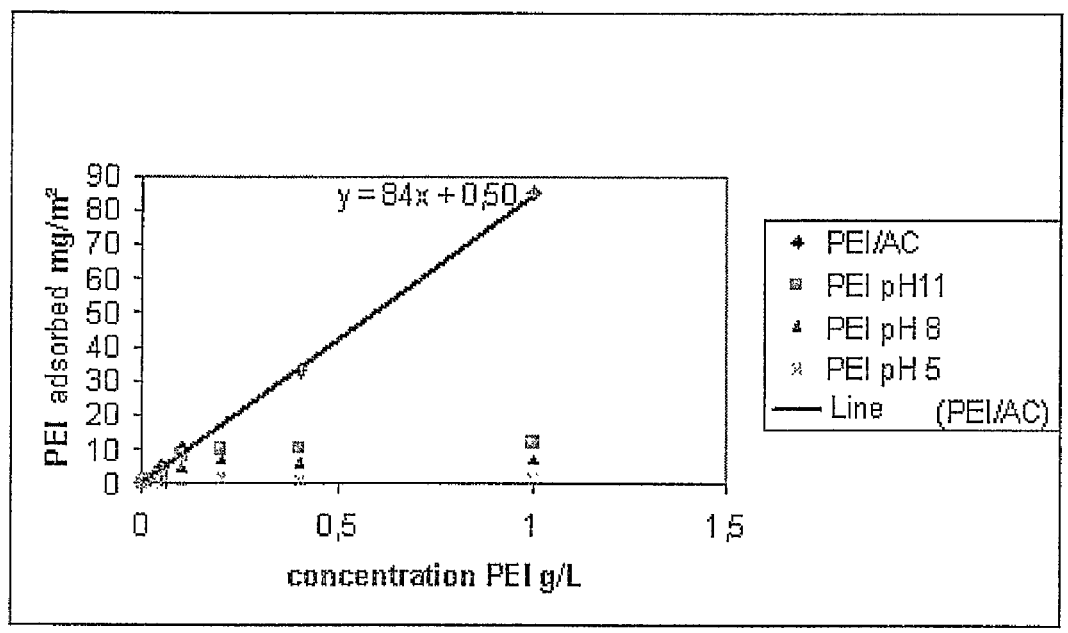
FIG. 10 shows the adsorption of PEI in mg/m$^2$ onto the surface of a support of the invention for various solutions of PEI at different concentrations and different pHs.

Adsorption of PEI in $mg/m^2$ onto the Surface of a Support:

FIG. 10 shows the adsorption of PEI in $mg/m^2$ onto the surface of a support for different solutions of PEI including a colloidal suspension of PEI at different pHs. The measured adsorption is that of PEI by circulation in the blood compartment of a dialyzer with a semi permeable membrane with hollow fibres of the FILTRAL type.

Adsorption depending on pH at the same concentration of PEI:

For the examples with a solution of PEI at a pH of 5 (adjusted with HCl), 8 (adjusted with NaOH) and 11 (adjusted with NaOH) respectively, it was observed that the adsorbed PEI did not exceed 10 $mg/m^2$. It was interesting to observe, as stated above, that the higher the pH (more basic), the greater the adsorption of PEI and this would lead the skilled person, for a solution with a given concentration of PEI, to use a high pH to adsorb more PEI.

Adsorption depending on the concentration of PEI for the same pH:

For the same pH, it was observed that when the concentration of the PEI solution increased, the adsorption of PEI increased, but not significantly. Adsorption of a colloidal solution of PEI mixed with citric acid:

In contrast, for a colloidal suspension of PEI mixed with citric acid (test mixture in a weight ratio of 1 for PEI and citric acid), it was surprisingly observed that the quantity of adsorbed PEI increased significantly with the concentration of PEI in the solution. Using a suspension of PEI mixed with citric acid (in acidic medium) increased the adsorption of PEI, although the skilled person would know that more PEI would be adsorbed by the membrane in a basic medium.

Conditions for Preparing a Cationic Polymer by Ultrafiltration:

FIG. 8 shows the procedure for preparing a cationic polymer such as polyethyleneimine by ultrafiltration, with the following steps:

a) preparation, in a tank, of a solution of 1.5 litres of a solution of PEI with a mass average molecular mass of 750 kdalton (LUPASOL P, BASF), 50 g per litre, in distilled water;

b) circulation, in a closed circuit, of said solution in the blood compartment of a hollow fibre dialyzer 2 (trade name FILTRAL 16, produced by GAMBRO INDUSTRIES, France) provided with a membrane (useful surface area 1.6 m$^2$) of AN69 (copolymer of acrylonitrile and sodium methallylsulphonate) at a flow rate of 300 ml per minute;

c) simultaneously with step b, ultrafiltration at a flow rate of 60 ml per minute with addition of water to the tank, at the same flow rate.

The preparation period was 156 minutes. An assay of the PEI present in the ultrafiltrate was determined in water by spectrophotometry after forming a coloured complex with cobalt II thiocyanate (maximum absorption at 304 nm).

Advantages:

The various advantages of the invention include:
- effective therapeutic treatment which is cheaper than known means for the treatment of septic syndrome, in particular by effective adsorption of mediators involved in septic syndrome (endotoxins, cytokines, anaphylatoxins, etc);
- improved purification of biological fluids such as blood, plasma or other liquids which may be injected into a patient;
- the anti-thrombogenic nature of the support which can avoid major systemic coagulation in the case of injecting anticoagulation agent during treatment via the membrane;
- the multifunctional nature of the support which is intended, if necessary at the same time, for the therapeutic treatment of septic syndrome and renal insufficiency (in particular by haemodialysis, ultrafiltration, haemofiltration and/or haemodiafiltration, etc);
- the reduction in the quantity of anticoagulation agents injected into the patient during an extracorporeal blood or plasma treatment session using a semi-permeable membrane and the exchanger;
- a reduction in the total quantity of anticoagulation agent(s) bound or not bound to the support necessary to carry out an extracorporeal blood or plasma treatment session and the subsequent reduction in the cost of the session and undesirable secondary effects due to the anticoagulation agent;
- improved action of the active principle (s) permanently bound to the support;
- improved haemodynamic condition in patients with septic syndrome;
- a larger quantity of the second polymer is grafted onto the membrane comprising the first polymer than that in WO-A-01/54802;
- a support constituted by a first polymer with a second polymer having a larger amount of free cationic or cationizable groups than in WO-A-01/54802 without necessarily using more polymer P2;
- possibility of grafting any polymer carrying cationic or cationizable groups onto the membrane without the necessity for a minimum size for that polymer, as is the case with the invention of WO-A-01/54802.

The invention claimed is:

1. Use of a suspension to treat a base support for medical use essentially constituted by a first polymer containing anionic or anionizable groups, including treating the base support with the suspension;
the suspension being in an acidic medium and comprising a second polymer containing cationic or cationizable groups which are capable of forming an ionic bond with the anionic or anionizable groups of the first polymer, the second polymer being in the colloidal form, the acidic medium further comprising at least one organic polyacid in association with the second polymer, allowing the second polymer to have said colloidal form.

2. Use according to claim 1, in which the organic polyacid is a polycarboxylic acid.

3. Use according to claim 2, in which the polycarboxylic acid comprises at least three carboxylic acid groups.

4. Use according to claim 2, in which the polycarboxylic acid is citric acid.

5. Use according to claim 2, in which the polycarboxylic acid comprises a tribasic organic acid.

6. Use according to claim 1, in which the second polymer is a cationic polymer selected from polyamines and polyimines.

7. Use according to claim 1, in which the anionic or anionizable groups of the first polymer are selected from sulphonic, phosphonic, carboxylic, sulphuric and phosphoric groups and salts of said groups.

8. Use according to claim 1, in which the anionic or anionizable groups of the first polymer are acidic sulphonic groups or sulphonic groups in their salt forms.

9. Use according to claim 1, in which the first polymer comprises a polyacrylonitrile.

10. Use according to claim 1, wherein treating the base support with the suspension comprises treating the surface of the base support with the suspension.

11. Use according to claim 1, wherein treating the base support with the suspension comprises treating the bulk of the base support with the suspension.

12. Use according to claim 1, in which the support base used is in the form of a semi permeable membrane, beads, a gel or a foam.

13. Use according to claim 1, in which the second polymer is a cationic polymer selected from cationic polyaminoacids.

14. Use according to claim 1, in which the second polymer is a cationic polymer selected from the group consisting of: polylysine, polyarginine, polyethyleneimine, copolymers thereof and mixtures thereof.

15. Use according to claim 1, in which the first polymer comprises a copolymer of acrylonitrile and sodium methallylsulphonate.

16. A composite support comprising a base support for the treatment of a biological fluid, in which:

the base support is essentially constituted by a first polymer carrying anionic or anionizable groups;

at least a part of the surface of the base support is coated with a second polymer ionically bonded to the first polymer, the second polymer carrying cationic or cationizable groups which are capable of forming an ionic bond with the anionic or anionizable groups of the first polymer; characterized in that the second polymer is in the colloidal form, allowing the composite membrane to adsorb at least one entity containing anionic or anionizable groups by bonding with cationic or cationizable groups of the second polymer, the second polymer being in association with an organic polyacid; wherein the composite support has an endotoxin adsorption capacity in aqueous medium of 500 UE/m$^2$ or more.

17. A composite support according to claim 16, in which the anionic or anionizable groups of the first polymer are selected from sulphonic, phosphonic, carboxylic, sulphuric, and phosphoric groups and salts of said groups, and wherein the second polymer is a cationic polymer selected from polyamines and polyimines.

18. A composite support according to claim 16, in which said part of the surface of the support, which is coated with the second polymer, is at least partially coated with at least one anticoagulation agent carrying anionic or anionizable groups which are capable of forming an ionic bond with the cationic or cationizable groups of the second polymer.

19. A composite support according to claim 18, in which the anticoagulation agent comprises at least one compound from the glycoaminoglycane family having an anticoagulation activity.

20. A composite support according to claim 18, in which the deposited surface concentration of the anticoagulation agent is in the range 1000 to 30000 IU/m$^2$ of membrane.

21. A composite support according to claim 18, in which the anticoagulation agent is selected from the group consisting of: non fractionated heparin, fractionated heparin, danaparoids, all heparin derivatives, and mixtures thereof.

22. A composite support according to claim 18, in which the deposited surface concentration of the anticoagulation agent is in the range 2000 to 8000 IU/m$^2$ of membrane.

23. A composite support according to claim 16, in which the surface concentration of the second polymer in the colloidal form is in the range 15 to 200 mg/m$^2$.

24. A composite support according to claim 23, in which the surface concentration of the second polymer in the colloidal form is in the range 15 to 100 mg/m$^2$.

25. A composite support according to claim 16, in which the second polymer comprises chains with a size sufficient not to traverse the base support.

26. A composite support according to claim 16, in which the second polymer is prepared by ultrafiltration of a solution of second polymer through a semi-permeable membrane to eliminate chains of the second polymer having a size below the size corresponding to the porosity of the base support.

27. A composite support according to claim 16, in which the base support is a semi-permeable membrane.

28. A composite support according to claim 27, in which the molecular mass of the second polymer is greater than the cutoff threshold of the semi-permeable membrane produced from the first polymer.

29. A composite support according to claim 27, in which the semi-permeable membrane is a stack in the form of planar membranes.

30. A composite support according to claim 16, for use in purification of blood or plasma by extracorporeal circulation, in which the base support is a semi-permeable membrane, the composite membrane comprising at least:
    a first surface intended to be brought into contact with the blood or plasma;
    a second surface intended to be brought into contact with a dialysate or a filtrate;
in which the first surface of the membrane is covered by the second polymer in the colloidal form and optionally by an anticoagulation agent carrying anionic or anionizable groups which are capable of forming an ionic bond with the cationic or cationizable groups of the second polymer.

31. A composite support according to claim 30, in which:
    the first surface of the membrane is covered by the anticoagulation agent carrying anionic or anionizable groups, which can form an ionic bond with the cationic or cationizable groups of the second polymer;
    the second surface of the membrane is covered by the second polymer in the colloidal form.

32. A composite support according to claim 30, in which at least the second surface of the membrane is covered by the second polymer in the colloidal form and optionally by an anticoagulation agent carrying anionic or anionizable groups, which can form an ionic bond with the cationic or cationizable groups of the second polymer.

33. A composite support according to claim 30, in which the semi-permeable composite membrane is constituted by a bundle of hollow fibres, and in which the interior surface of the hollow fibres is the first surface intended to be brought into contact with the blood or the plasma and in which the exterior surface of the hollow fibres is the second surface intended to be brought into contact with the filtrate or the dialysate.

34. A composite support according to claim 16, in which the base support is constituted by one of the following forms: an assembly of beads, a foam or a gel.

35. A composite support according to claim 34, in which the base support has a variable porosity.

36. A composite support according to claim 16, in which the second polymer in the colloidal form is present in the bulk of the support.

37. A composite support according to claim 16, in which the adsorption capacity of the endotoxins is in the range 2000 to 5000 UE/m$^2$.

38. An exchanger comprising:
    a housing defining a first compartment and a second compartment;
    the first compartment being provided with an inlet and an outlet and intended for the circulation of biological liquid to be treated;
    the second compartment being intended for the circulation of dialysate or filtrate and being provided with an outlet and optionally with an inlet; the two compartments being separated by a composite support according to claim 16.

39. A device for adsorption of entities contained in a biological fluid, comprising:
    a housing provided with an inlet and an outlet and intended for the circulation of biological liquid to be treated;
    a composite support according to claim 16 contained in the housing.

40. A method of treating a biological fluid comprising a step of contacting the biological fluid with a support according to claim 16 to remove endotoxins from the biological fluid and thereby treat septic syndrome.

41. A method of purifying in blood or plasma comprising a step of contacting the blood or plasma during extracorporeal circulation with a support according to claim 16 and thereby removing certain molecules from the blood or plasma.

42. A method of treating blood or plasma to reduce its tendency to coagulate comprising a step of contacting the blood or plasma with a support according to claim 16 and thereby reducing the blood or plasma's tendency to coagulate and thereby reducing the amount of anticoagulation agent needed systemically by a patient during an extracorporeal blood treatment session.

43. A composite support according to claim 16, in which the anionic or anionizable groups of the first polymer are selected from sulphonic, phosphonic, carboxylic, sulphuric, and phosphoric groups and salts of said groups, and wherein the second polymer is a cationic polymer selected from cationic polyaminoacids.

44. A composite support according to claim 16, in which the anionic or anionizable groups of the first polymer are selected from sulphonic, phosphonic, carboxylic, sulphuric, and phosphoric groups and salts of said groups, and wherein the second polymer is a cationic polymer selected from the group consisting of: polylysine, polyarginine, polyethyleneimine, copolymers thereof and mixtures thereof.

45. A composite support according to claim 16, characterized by an endotoxin adsorption capacity in aqueous medium of 1500 UE/m$^2$ or more for a membrane.

46. A method for manufacturing a composite support for the treatment of biological fluid, said method comprising the following steps:
   a) providing a base support essentially constituted by a first polymer carrying anionic or anionizable groups;
   b) providing a suspension in an acidic medium comprising a second polymer carrying cationic or cationizable groups which are capable of forming an ionic bond with the anionic or anionizable groups of the first polymer, the second polymer being in the colloidal form;
   c) bringing the suspension into contact with at least a portion of the surface of the base support, wherein
the anionic or anionizable groups of the first polymer are selected from sulphonic, phosphonic, carboxylic, sulphuric, and phosphoric groups and salts of said groups, and wherein the second polymer is a cationic polymer selected from polyamines and polyimines, and
the second polymer is obtained in the colloidal form by a step for mixing a first solution comprising the second polymer with a second solution comprising at least one organic polyacid.

47. A method according to claim 46, in which the organic polyacid is a polycarboxylic acid.

48. A method according to claim 47, in which the ratio of the concentration of the second polymer in the suspension to the concentration of organic polyacid in the suspension is such that it can produce a suspension in the colloidal form.

49. A method according to claim 48, in which the second polymer is polyethyleneimine and the polyacid is citric acid, said ratio of the concentration of polyethyleneimine and citric acid being in the range 0.9 to 1.1.

50. A method according to claim 46, the method comprising, after step c), as step d) as follows: bringing at least a portion of said part of the surface of the base support into contact with a solution comprising at least one anticoagulation agent carrying anionic or anionizable groups which can form an ionic bond with the cationic or cationizable groups of the second polymer to bind an anticoagulation coating onto said portion of the part of the surface of the support coated with the second polymer.

51. A method according to claim 50, in which step d) is carried out just before use of a composite support for the treatment of a composite biological fluid or during the manufacture of the composite support.

52. A method according to claim 46, comprising as the ultimate step, manufacturing step for sterilization of the support.

53. A method according to claim 52, wherein sterilization of the support comprises sterilization with gamma irradiation, sterilization with ethylene oxide, or sterilization with ethylene oxide preceded by gamma irradiation.

54. A method according to claim 46, in which the first solution comprising the second polymer is prepared by ultrafiltration of a solution of second polymer through a semipermeable membrane to eliminate chains of the second polymer having a size which is less than or equal to the size corresponding to the porosity of the base support.

55. A method according to claim 46, in which the treatment with the suspension in an acid medium of the second polymer in the colloidal form is carried out in at least a portion of the bulk of the base support.

56. A method according to claim 46, wherein the second polymer is a cationic polymer selected from cationic polyaminoacids.

57. A method according to claim 46, wherein the second polymer is a cationic polymer selected from the group consisting of: polylysine, polyarginine, polyethyleneimine, copolymers thereof and mixtures thereof.

58. A method for manufacturing an exchanger for the treatment of a biological liquid, the exchanger comprising a housing defining a first compartment and a second compartment, the first compartment being provided with an inlet and an outlet and being intended for the circulation of biological liquid to be treated, the second compartment being intended for the circulation of dialysate or filtrate and being provided with an outlet and optionally with an inlet, the two compartments being separated by a base support, the method comprising the following steps:
   a1) providing the base support essentially constituted from a first polymer carrying anionic or anionizable groups;
   a2) assembling the various components of the exchanger, including mounting the base support in the housing;
   b1) providing a suspension in an acidic medium containing a second polymer carrying cationic or cationizable groups which can form an ionic bond with the anionic or anionizable groups of the first polymer, the second polymer being in the colloidal form;
   b2) bringing the suspension into contact with at least a first portion of the surface of the base support intended to be brought into contact with the liquid to be treated;
   b3) in the case in which steps (b1-b2) are carried out after step a2), rinsing and/or purging the exchanger of the solution containing the second polymer;
   c1) optionally, sterilizing the exchanger thus obtained, wherein
the anionic or anionizable groups of the first polymer are selected from sulphonic, phosphonic, carboxylic, sulphuric, and phosphoric groups and salts of said groups, and wherein the second polymer is a cationic polymer selected from polyamines and polyimines.

59. A method according to claim 58, comprising, after steps b1) to b3), a step c0) for bringing at least one solution of an anticoagulation agent into contact in a liquid medium with at least a portion of the part of the surface of the base support coated with the second polymer in the colloidal form to bind an anticoagulating coating onto the surface of the support coated with second polymer in the colloidal form; step c0) may be carried out before or after step a2).

60. A method according to claim 58, wherein the second polymer is a cationic polymer selected from cationic polyaminoacids.

61. A method according to claim 58, wherein the second polymer is a cationic polymer selected from the group consisting of: polylysine, polyarginine, polyethyleneimine, copolymers thereof and mixtures thereof.

62. A method for manufacturing a medical device for the adsorption of entities contained in a biological liquid for the treatment of a biological liquid, the device comprising a housing provided with an inlet and an outlet and being intended for the circulation of biological liquid to be treated, a composite support according to claim 16, the method comprising the following steps:

a1) providing a base support essentially constituted from a first polymer carrying anionic or anionizable groups;

a2) assembling the various components of the device, including mounting the base support in the housing;

b1) providing a suspension in an acidic medium containing a second polymer carrying cationic or cationizable groups which can form an ionic bond with the anionic or anionizable groups of the first polymer, the second polymer being in the colloidal form;

b2) bringing the suspension into contact with at least a first portion of the base support intended to be brought into contact with the liquid to be treated;

b3) in the case in which steps (b1-b2) are carried out after step a2), rinsing and/or purging the adsorption device of the solution containing the second polymer;

c1) optionally, sterilizing the exchanger thus obtained.

\* \* \* \* \*

UNITED STATES PATENT AND TRADEMARK OFFICE
CERTIFICATE OF CORRECTION

PATENT NO. : 8,137,562 B2  Page 1 of 1
APPLICATION NO. : 12/305362
DATED : March 20, 2012
INVENTOR(S) : Michel Thomas It is certified that error appears in the above-identified patent and that said Letters Patent is hereby corrected as shown below:

At column 24, line 64, claim 41, after "purifying" please delete "in".

Signed and Sealed this
Twenty-sixth Day of June, 2012

David J. Kappos
*Director of the United States Patent and Trademark Office*